United States Patent
Stürmer et al.

(10) Patent No.: US 7,795,004 B2
(45) Date of Patent: Sep. 14, 2010

(54) PROCESS FOR THE RACEMIZATION OF OPTICALLY ACTIVE SECONDARY ALCOHOLS WITH THE USE OF TWO ALCOHOL DEHYDROGENASES

(75) Inventors: Rainer Stürmer, Rödersheim-Gronau (DE); Wolfgang Kroutil, Graz (AT); Kurt Faber, Graz (AT); Christian Gruber, Graz (AT)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/297,804

(22) PCT Filed: Apr. 19, 2007

(86) PCT No.: PCT/EP2007/053858
§ 371 (c)(1),
(2), (4) Date: Oct. 20, 2008

(87) PCT Pub. No.: WO2007/122182
PCT Pub. Date: Nov. 1, 2007

(65) Prior Publication Data
US 2009/0098623 A1    Apr. 16, 2009

(30) Foreign Application Priority Data
Apr. 21, 2006    (EP)    ................... 06112908

(51) Int. Cl.
*C12P 41/00*    (2006.01)

(52) U.S. Cl. ....................................................... 435/280
(58) Field of Classification Search ....................... None
See application file for complete search history.

(56) References Cited

FOREIGN PATENT DOCUMENTS

WO    WO-2006/021885 A1    3/2006

OTHER PUBLICATIONS

Ludwig et al., :A Long-Chain Secondary Alcohol Dehydrogenase from *Rhodococcus erythropolis* ATCC 4277, Applied and Environmental Microbiology 61 (10) : 3729-3733 (1995).*
Lutstorf et al., "Multiple forms of alcohol dehydrogenase in *Sacharomyces cerevisiae*. I. Physiological control of ADH-2 and properties of ADH-2 and ADH-4", Archives Biochem. Biophys. 126 (3) : 933-44 (1968), abstract only.*
Strauss, U.T., et al., "Biocatalytic transformation of racemates into chiral building blocks in 100% chemical yield and 100% enantiomeric excess," Tetrahedron: Assymmetry, 1999, vol. 10, pp. 107-117.
Heidlas, J., et al., "Enantioselectivities of enzymes involved in the reduction of methylketones by Bakers' yeast," Enzyme Microb. Technol., 1991, vol. 13, pp. 817-821.

* cited by examiner

*Primary Examiner*—Sandra E Saucier
(74) *Attorney, Agent, or Firm*—Connolly Bove Lodge & Hutz LLP

(57) ABSTRACT

A method for racemizing optically active secondary alcohols by incubating these alcohols with at least one alcohol dehydrogenase of the E.C. 1.1.1. class.

2 Claims, No Drawings

PROCESS FOR THE RACEMIZATION OF OPTICALLY ACTIVE SECONDARY ALCOHOLS WITH THE USE OF TWO ALCOHOL DEHYDROGENASES

RELATED APPLICATIONS

This application is a national stage application (under 35 U.S.C. §371) of PCT/EP2007/053858, filed Apr. 19, 2007, which claims benefit of European Application No. 06112908.6, filed Apr. 21, 2006.

DESCRIPTION

The present invention relates to a method for enzymatic racemization of optically active secondary alcohols.

PRIOR ART

Secondary alcohol dehydrogenases catalyze the oxidation of secondary alcohols and the reduction of the corresponding ketone to the alcohol.

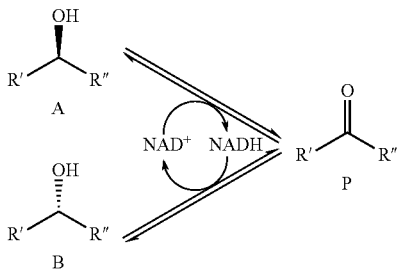

The present invention relates to a method for racemizing optically active secondary alcohols by incubating these alcohols with at least one alcohol dehydrogenase of the E.C. 1.1.1. class.

Optically active secondary alcohols which can be employed in the method of the invention include a large number of structurally different alcohols and compounds comprising secondary alcohol groups.

Aliphatic alcohols having a chain length of from 4 to about 20 C atoms are suitable, it being possible for the aliphatic radical to be branched or unbranched, mono- or polyunsaturated or else cyclic or to form parts of a cyclic system, for example a heterocyclic system such as morpholine, pyrrole, thiophene, pyrazole, imidazole, oxazole, thiazole, pyridine, pyran, pyrimidine, pyridazine, pyrazine, coumarone, indole, quinoline.

Preferred aliphatic alcohols are 2-butanol, 2-pentanol, 2-hexanol, 3-hexanol, 2-heptanol, 3-heptanol, 2-octanol, 3-octanol, 2-nonanol, 2-decanol.

Further suitable secondary alcohols are those having an aryl-alkyl structure, it being possible for the aromatic moiety to be homoaromatic or heteroaromatic.

Preferred alcohols are those which have an optionally substituted phenyl, naphthyl, pyridyl group as aromatic moiety.

Particularly preferred secondary alcohols are optionally substituted phenylethanol-2, phenylpropanol-2, phenylbutanol-2, phenylpentanol-2, phenylhexanol-2.

The alcohols may also be substituted one or more times, i.e. one or more H atoms are by groups such as F, Cl, Br, I, $NH_2$, NHR, $NR_2$, SH, CN, COOH, COOR, CO, CS, CNH, $NO_2$, in which R may be alkyl or alkylaryl radicals.

Suitable as alcohol dehydrogenase are NAD- or NADP-dependent oxidoreductases of enzyme classification E.C. 1.1.1., in particular alcohol dehydrogenases, preferably those which have been isolated from microorganisms or have been isolated and/or modified from such by means of genetic manipulation methods. The modification can be introduced either by so-called random mutagenesis methods or by so-called site-specific mutagenesis.

Alcohol dehydrogenases preferably used are those from microorganisms of the genus *Lactobacillus*, especially of the species *Lactobacillus kefir*, and those of the genus *Rhodococcus*, especially of the species *Rhodococcus erythropolis*.

These alcohol dehydrogenases are commercially available (e.g. from Fluka) or can be acquired from collections of strains accessible to the public and be isolated by known methods. For example *Lactobacillus kefiri* DSM 20587, ATCC 35411; *Rhodococcus erythropolis* DSM 43066, ATCC 25544.

In a preferred embodiment, a plurality of different alcohol dehydrogenases is used as alcohol dehydrogenases, preferably those differing in Prelog specificity, particularly preferably an alcohol dehydrogenase having Prelog specificity and a second alcohol dehydrogenase having anti-Prelog specificity. For the definition of Prelog specificity, reference is made to the document by Kurt Faber, Pure Appl. Chem. 69, 1613-1632, 1997, especially the section on redox reactions, which is expressly incorporated herein by reference.

Thermodynamic considerations indicate that racemization is possible with any alcohol dehydrogenase. The alcohol dehydrogenase employed for the racemization ought to have a minimal enantio/stereoselectivity both for the oxidation and for the reduction, in order to achieve a maximal racemization rate. Since the selectivity is inter alia a function of temperature, racemization is likewise possible at elevated temperature using an enzyme which is selective under "normal" conditions (e.g. *L. kefir* alcohol dehydrogenase) if the activity is not lost under these conditions. Alcohol dehydrogenases having a high enantio- and stereoselectivity (E>200) show a slow racemization activity.

In two- or multi-enzyme systems, the selectivity of the alcohol dehydrogenase system is composed of the selectivities of the enzymes employed. On simultaneous use of a 'Prelog' enzyme (*R. erythropolis* alcohol dehydrogenase) and of an anti-'Prelog' enzyme (*L. kefir* alcohol dehydrogenase), each of which has a high substrate-related enantio- or stereoselectivity but have opposite stereopreference, the overall selectivity of the system is 1 and the racemization is speeded up.

The enzymes having dehydrogenase activity which are used according to the invention can be used in the method of the invention as free or immobilized enzyme.

The method of the invention is advantageously carried out at a temperature between 0° C. to 95° C., preferably between 10° C. to 85° C., particularly preferably between 15° C. to 75° C.

The pH in the method of the invention is advantageously maintained at between pH 4 and 12, preferably between pH 4.5 and 9, particularly preferably between pH 5 and 8.

The method of the invention can be carried out, depending on the substrate, in an additional solvent or in the substrate itself as solvent. Suitable solvents are all conventional organic solvents which permit an enzymatic redox reaction, especially alcohols, ketones, ethers, hydrocarbons or mixtures of these substances. The chosen solvents advantageously allow easy removal of the racemic secondary alcohol.

By optically active alcohols are meant in the method of the invention enantiomers which show an enantiomeric enrichment. The enantiomeric purities preferably used in the method are at least 70% ee, preferably min. 80% ee, particularly preferably min. 90% ee, very particularly preferably min. 98% ee.

By racemization of optically active alcohols is meant in this connection a reduction in the enantiomeric purity compared with the initial alcohol (substrate), especially a reduction in the enantiomeric purity by 10, 20, 25, 30 percent. Racemization is not to be understood to mean the categoric necessity for the ratio of the enantiomers to reach 50:50, although this complete racemization represents a preferred embodiment of the invention.

The amount of cofactor (NAD/NADH or NADP/NADPH) employed is immaterial for the racemization as long as it is ensured that at least one mole of $NAD^+$ or NADP is present per mole of enzyme, in order to ensure complete formation of the enzyme-cofactor complex. The concentration of ketone formed as intermediate is controlled by the $NAD^+$/NADH ratio employed and by the alcohol/ketone redox potential.

The method of the invention can also advantageously be coupled to cofactor-regeneration systems.

The method of the invention can be operated both continuously and batchwise.

Experimental Section

Alcohols Used (Substrate)

| Number | Name | Structure |
|---|---|---|
| 1 | 2-Octanol | $H_3C$—CH(OH)—$C_6H_{13}$ |
| 2 | 2-Heptanol | $H_3C$—CH(OH)—$C_5H_{11}$ |
| 3 | 2-Nonanol | $H_3C$—CH(OH)—$C_7H_{16}$ |
| 4 | 1-Phenyl-2-propanol | (phenyl-CH2-CH(OH)-CH3) |
| 5 | 6-Methyl-5-hepten-2-ol | (structure) |

Enzymes Used

| Abbreviation | Name | Source |
|---|---|---|
| LK alcohol dehydrogenase | *Lactobacillus kefir* alcohol dehydrogenase | commercial Fluka 05643 |
| RE alcohol dehydrogenase | *Rhodococcus erythropolis* alcohol dehydrogenase | commercial Jülich Fine Chemicals 04.11 |

Enzymes Used

| Enzyme stock solutions | Concentration | U/mL |
|---|---|---|
| LK alcohol dehydrogenase | 8 mg/ml | 3 |
| RE alcohol dehydrogenase | 80 mg/ml | 3 |
| RE alcohol dehydrogenase & | 4 mg/mL | 1.5 |
| LK alcohol dehydrogenase | 40 mg/mL | 1.5 |

50 µl of enzyme stock solution were dissolved in 500 µl of phosphate buffer (50 mM, pH 7.5) in a 2 ml Eppendorf® vessel, and 10 µl of $NAD^+$/NADH stock solution (50 mg NADH/ml, 30 mg $NAD^+$/ml) were added. The reaction was then started by adding 2 µl of substrate (48 h, 30° C./65° C., 130 rpm). The reaction was stopped by extraction with 500 µl of EtOAc.

One-Enzyme System

| Substrate | e.e. of substrate[a] [%] | Enzyme | Temperature [° C.] | Ketone [%] | e.e.[a,b] [%] |
|---|---|---|---|---|---|
| (R)-1 | >−99.9 | RE alcohol dehydrogenase | 30 | <0.1 | −98.35 |
| | | LK alcohol dehydrogenase | 30 | 22.61 | −98.04 |
| | | LK alcohol dehydrogenase | 65 | <0.1 | −4.53 |
| (S)-1 | >99.9 | RE alcohol dehydrogenase | 30 | 0.25 | 99.53 |
| | | LK alcohol dehydrogenase | 30 | 0.00 | >99.9 |
| (R)-2 | >−99.9 | RE alcohol dehydrogenase | 30 | n.d. | <−99.9 |
| | | LK alcohol dehydrogenase | 30 | n.d. | <−99.9 |
| (R)-3 | >−99.9 | RE alcohol dehydrogenase | 30 | 1.67 | −97.54 |
| | | LK alcohol dehydrogenase | 30 | 27.30 | −93.04 |
| (S)-4 | >99.9 | RE alcohol dehydrogenase | 30 | 3.12 | >99.9 |
| | | LK alcohol dehydrogenase | 30 | 3.63 | >99.9 |
| (R)-5 | >−99.9 | RE alcohol dehydrogenase | 30 | 0.56 | −98.12 |
| | | LK alcohol dehydrogenase | 30 | 24.38 | −73.94 |

[a]Positive and negative e.e. values relate to the excess of the respective (S) and (R) enantiomer.
[b]e.e. after a reaction time of 48 h.

Two-Enzyme System

| Substrate | e.e. of substrate[a] [%] | Enzyme | Temperature [° C.] | Ketone [%] | e.e.[a,b] [%] |
|---|---|---|---|---|---|
| (R)-1 | >−99.9 | RE alcohol dehydrogenase & LK alcohol dehydrogenase | 30 | 2.23 | −9.49 |
| (S)-1 | >99.9 | RE alcohol dehydrogenase & LK alcohol dehydrogenase | 30 | 3.35 | 36.95 |
| (R)-2 | >−99.9 | RE alcohol dehydrogenase & LK alcohol dehydrogenase | 30 | n.d. | −40.21 |

-continued

| Substrate | e.e. of substrate[a] [%] | Enzyme | Temperature [° C.] | Ketone [%] | e.e.[a,b] [%] |
|---|---|---|---|---|---|
| (R)-3 | >−99.9 | RE alcohol dehydrogenase & LK alcohol dehydrogenase | 30 | 2.57 | −32.19 |
| (S)-4 | >99.9 | RE alcohol dehydrogenase & LK alcohol dehydrogenase | 30 | 23.12 | >99.9 |
| (R)-5 | >−99.9 | RE alcohol dehydrogenase & LK alcohol dehydrogenase | 30 | 5.74 | −23.92 |

[a]Positive and negative e.e. values relate to the excess of the respective (S) and (R) enantiomer.
[b]e.e. after a reaction time of 48 h.

Analyses

GC Analyses

Gas chromatograph: Variant 3900 gas chromatograph (FID)
Column: Chrompack Chirasil-DEX CB (25 m×0.32 mm×0.25 μm, 1.0 bar H$_2$)

| Substr. | GC column | Temperature program[a] | Retention time [min] | e.e.[b] [%] |
|---|---|---|---|---|
| 2 | Chirasil-DEX CB | 110/0/2.5/120/0/ 10/200/0 | (S) 1.369 (R) 1.434 Ketone n.d. | >99.9 <−99.9 — |
| 3 | Chirasil-DEX CB | 110/0/2.5/120/0/ 10/200/0 | (S) 2.741 (R) 2.988 Ketone 1.795 | >99.9 <−99.9 — |
| 4 | Chirasil-DEX CB | 110/0/2.5/120/0/ 10/200/0 | (S) 3.683 (R) n.d. Ketone 2.65 | >99.9 <−99.9 — |
| 5 | Chirasil-DEX CB | 110/0/2.5/120/0/ 10/200/0 | (S) 1.860 (R) 1.981 Ketone 1.303 | >99.9 <−99.9 — |

[a]° C./holding time [min]/heating rate [° C./min]/° C./holding time [min]/heating rate/° C./holding time [min],
[b]Positive and negative e.e. values relate to the excess of the respective (S) and (R) enantiomer.
n.d.: not detectable Acetylation of Alcohols (General Method)

The derivatization was carried out by adding 100 μl of acetic anhydride/DMAP solution and incubating at 30° C./130 rpm for 60 min. 0.5 ml of H2O was added.

The organic phase was removed and dried over Na2SO4.

We claim:

1. A method for racemizing optically active secondary alcohols comprising incubating said optically active secondary alcohols with at least one alcohol dehydrogenase of the E.C. 1.1.1. class, wherein said at least one alcohol dehydrogenase of the E.C. 1.1.1. class comprises a mixture of two alcohol dehydrogenases, and wherein one alcohol dehydrogenase of said mixture has a Prelog specificity and the other alcohol dehydrogenase of said mixture has an anti-Prelog specificity.

2. The method of claim 1, wherein said incubation is performed in the absence of organic solvents.

* * * * *